United States Patent
Huseynov et al.

(10) Patent No.: US 9,506,833 B2
(45) Date of Patent: Nov. 29, 2016

(54) ULTRASONIC GAS LEAK DETECTORS AND TESTING METHODS

(71) Applicant: General Monitors, Inc., Lake Forest, CA (US)

(72) Inventors: Javid Huseynov, Fountain Valley, CA (US); Shankar B. Baliga, Irvine, CA (US)

(73) Assignee: General Monitors, Inc., Lake Forest, CA (US)

( * ) Notice: Subject to any disclaimer, the term of this patent is extended or adjusted under 35 U.S.C. 154(b) by 174 days.

(21) Appl. No.: 14/336,399

(22) Filed: Jul. 21, 2014

(65) Prior Publication Data

US 2015/0276540 A1    Oct. 1, 2015

Related U.S. Application Data

(60) Provisional application No. 61/970,808, filed on Mar. 26, 2014.

(51) Int. Cl.
| | | |
|---|---|---|
| *G01N 21/00* | (2006.01) | |
| *G01M 3/00* | (2006.01) | |
| *G01M 3/24* | (2006.01) | |
| *G01N 29/14* | (2006.01) | |

(52) U.S. Cl.
CPC ............. *G01M 3/007* (2013.01); *G01M 3/24* (2013.01); *G01N 29/14* (2013.01)

(58) Field of Classification Search
CPC ...... G01M 3/24; G01M 3/243; G01N 29/14; G01N 29/46; G01N 33/0006; G01N 33/007; G01N 27/4163; B29C 66/71; F02D 41/1495; F02D 41/222

USPC .......................................................... 73/1.06
See application file for complete search history.

(56) References Cited

U.S. PATENT DOCUMENTS

| | | |
|---|---|---|
| 4,287,581 A | 9/1981 | Neale, Sr. |
| 4,333,028 A | 6/1982 | Panton |
| 4,704,709 A | 11/1987 | Slebzak et al. |

(Continued)

FOREIGN PATENT DOCUMENTS

| | | |
|---|---|---|
| EP | 1522839 | 4/2005 |
| EP | 1522839 A1 | 4/2005 |

OTHER PUBLICATIONS

International Search Report and Written Opinion of the International Searching Authority, re International application No. PCT/US2015/016966, mailed Jun. 5, 2015.

*Primary Examiner* — Eric S McCall
*Assistant Examiner* — Mohammed E Keramet-Amircolai
(74) *Attorney, Agent, or Firm* — Larry K. Roberts

(57) ABSTRACT

An ultrasonic gas leak detector and test method, configured to discriminate the ultrasound generated by a pressurized gas leak into the atmosphere from ultrasound generated by man-made ultrasonic sources. In an exemplary embodiment an ultrasonic gas leak detector is able to identify a remote ultrasonic test source as a known test source and to initiate a test sequence instead of alarm. An output function generates detector outputs in dependence on the test mode initiation. The ultrasonic gas leak detector may also identify various other man-made ultrasonic sources as being neither gas leaks nor remote test sources but as nuisance or hostile sources to be identified as such. The test method utilizes a narrowband test source at a known ultrasonic frequency to ensonify the detector.

18 Claims, 8 Drawing Sheets

(56) References Cited

U.S. PATENT DOCUMENTS

| | | |
|---|---|---|
| 5,401,174 A | 3/1995 | Hansen |
| 5,452,267 A | 9/1995 | Spevak |
| 5,561,290 A | 10/1996 | Strobel et al. |
| 5,610,876 A | 3/1997 | Jeffers |
| 5,726,952 A | 3/1998 | Eckert et al. |
| 6,617,848 B2 | 9/2003 | Abe |
| 6,647,762 B1 | 11/2003 | Roy |
| 7,081,699 B2 | 7/2006 | Keolian et al. |
| 7,126,878 B1 | 10/2006 | Erikson |
| 7,227,294 B2 | 6/2007 | Mazz et al. |
| 7,318,335 B2 | 1/2008 | Olesen et al. |
| 2006/0191341 A1* | 8/2006 | Olesen ............... G01M 3/243 73/592 |
| 2009/0060246 A1 | 3/2009 | Baliga et al. |
| 2012/0194973 A1 | 8/2012 | Baliga et al. |
| 2013/0166227 A1* | 6/2013 | Hermann ............ G01N 29/30 702/51 |

* cited by examiner

ULTRASONIC GAS LEAK DETECTORS AND TESTING METHODS

BACKGROUND

Ultrasonic gas leak detectors measure the sound pressure waves generated by the turbulent flow when gas escapes from higher pressures to the ambient atmosphere. Such gas leak detectors are used as industrial safety devices to monitor the unwanted or unexpected release of combustible or toxic gases into the atmosphere. The leaks need to be identified quickly before they grow further in magnitude, to allow for timely remedial action to be taken. A drawback of conventional ultrasonic gas leak detectors that depend on thresholds and time delays for their functionality is the inability to effectively verify their performance in the field, and to conduct functional safety checks at proof test intervals. Proof testing is a requirement of safety instrumented systems to demonstrate that everything is working and performing as expected. Conventional ultrasonic gas leak detectors are unable to differentiate between the sound emitted by a real gas release and a remote ultrasonic test source to be used for periodic system performance check. This is a major inconvenience to the industrial facility that leads to either the bypassing of critical proof testing or a significant operating cost burden. Conventional ultrasonic gas leak detectors provide maintenance personnel with no means to functionally remote test the gas leak detector without the disruption caused by the need to disable alarms.

SUMMARY

An exemplary embodiment of a method of testing an ultrasonic gas leak detector includes operating the gas leak detector in an operating mode, wherein the gas leak detector is responsive to broadband ultrasonic sound generated by a pressurized gas leak to initiate an alarm mode; ensonifying the gas leak detector with ultrasonic energy from a remote test source which is different from the broadband ultrasonic sound generated by a real gas leak; processing the received ultrasonic energy to determine if measured characteristics of the ultrasonic energy correspond to predetermined characteristics of a predetermined test signal from a test source; and operating the gas leak detector in a test mode if the processing indicates the received ultrasonic energy is a test signal from the test source.

An exemplary embodiment of an ultrasonic gas leak detector is configured to discriminate the ultrasound generated by a pressurized gas leak into the atmosphere from ultrasound generated by man-made ultrasonic sources, and includes an ultrasonic microphone system responsive to received ultrasonic energy to generate microphone signals, a processor system configured to process digitized versions of the microphone signals, and in an operating mode, to process the digitized versions to detect pressurized gas leaks and initiate an alarm mode upon detection. The processor system is further configured to identify unique ultrasonic test signals from a remote ultrasonic test source as a known test source and to initiate a test mode in response to the identification instead of entering an alarm mode. The processor system is configured to provide an output function to generate detector outputs in dependence on the test mode initiation.

BRIEF DESCRIPTION OF THE DRAWINGS

Features and advantages of the disclosure will readily be appreciated by persons skilled in the art from the following detailed description when read in conjunction with the drawings wherein.

DETAILED DESCRIPTION

Figure 1A:
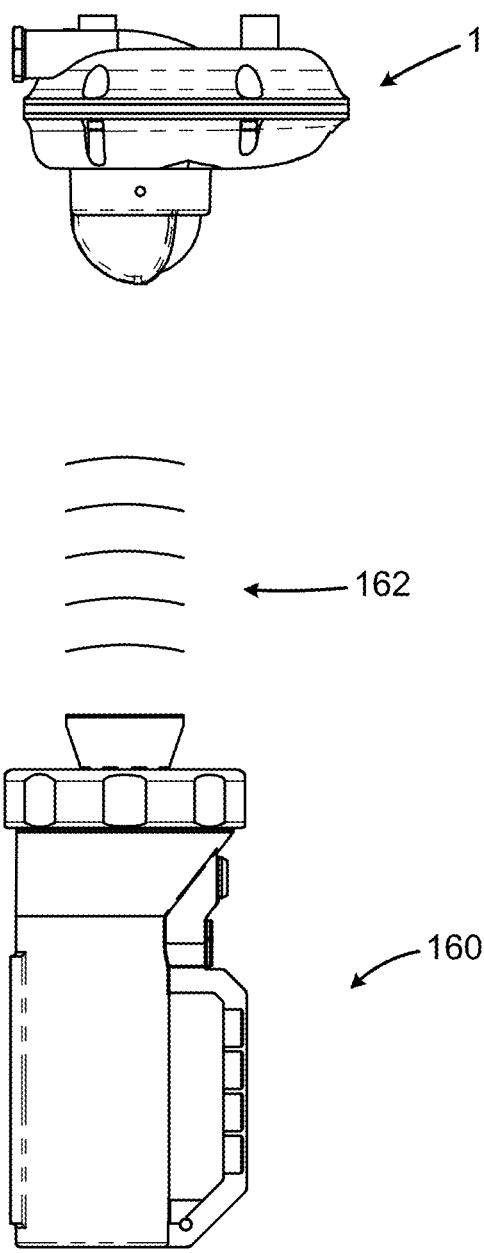
FIG. 1A illustrates an exemplary setup of an ultrasonic gas leak detector ensonified with, i.e. subjected to sound from, a remote ultrasonic tester along the axis of the ultrasonic gas leak detector.

In the following detailed description and in the several figures of the drawing, like elements are identified with like reference numerals. The figures are not to scale, and relative feature sizes may be exaggerated for illustrative purposes.

Figure 1B:
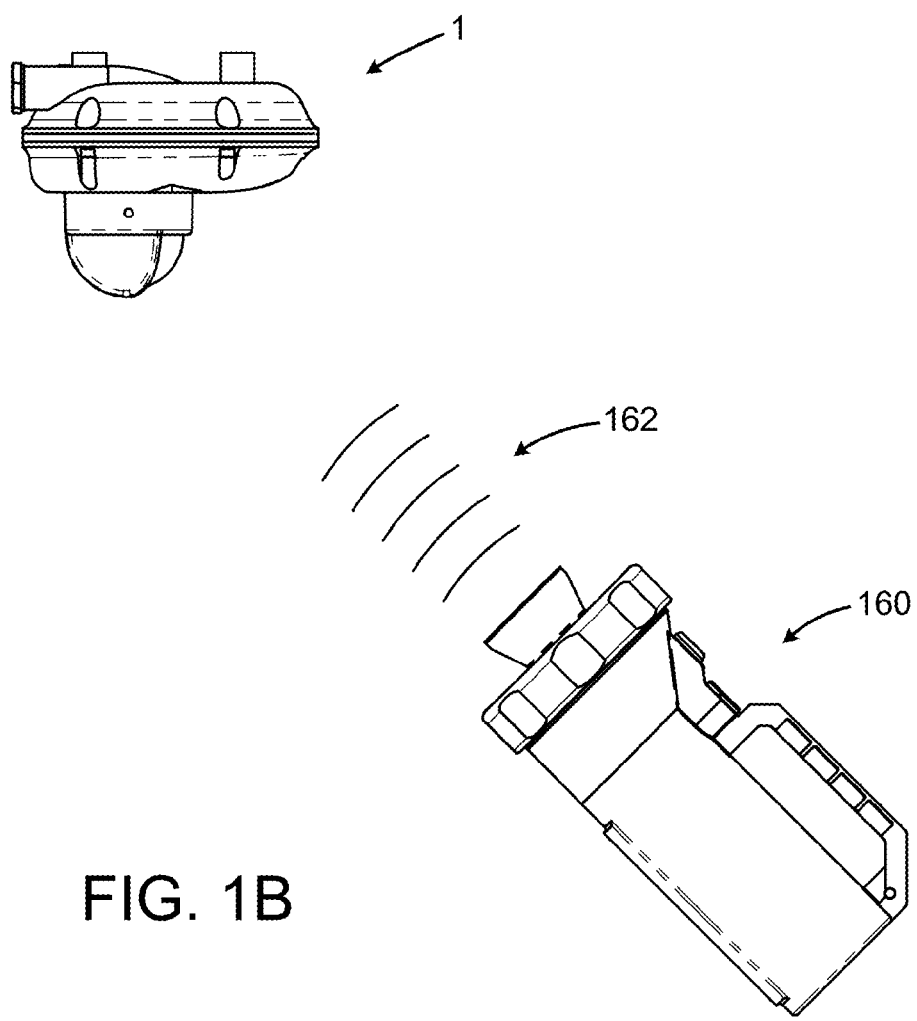
FIG. 1B illustrates an exemplary setup of an ultrasonic gas leak detector ensonified with a remote ultrasonic tester at an angle to the axis of the ultrasonic gas leak detector.

FIG. 1A illustrates an ultrasonic gas leak detector 1 for use in hazardous locations ensonified with ultrasonic energy from a remote ultrasonic test source 160 along the axis of the ultrasonic gas leak detector. As used herein, "ensonify" means to purposefully subject the ultrasonic gas leak detector to a sound pressure level. The ultrasonic gas leak detector 1 in this example includes an ultrasonic sensing microphone 2 (FIG. 2), and is typically mounted with the ultrasonic sensing microphone 2 facing downward. The ultrasonic gas leak detector 1 responds to the sound energy 162 from the ultrasonic source 160 with an increase in measured sound pressure level (SPL). FIG. 1B illustrates the ultrasonic gas leak detector 1 ensonified with ultrasonic energy 162 from test source 160 at an angle to the axis of the ultrasonic gas leak detector. Again, the ultrasonic gas leak detector 1 responds to the ultrasonic test source 160 by measuring an increased sound pressure level (SPL). In a functional test, the operator would typically walk around and remote test the ultrasonic gas leak detector from different directions. In one exemplary embodiment, the alarm threshold of the ultrasonic gas leak detector may typically be set at 79 decibels (dB); lower thresholds may be used in locations with low ultrasonic background.

A need exists to enable the ultrasonic gas leak detector to uniquely identify the sound from a remote ultrasonic test source as being different from the broadband ultrasonic sound generated by a real pressurized gas leak, thereby initiating a test sequence as opposed to entering alarm. The ultrasonic gas leak detector could also be configured to reject sound from other unique narrowband ultrasonic nuisance sources such as electronic dog whistles operating in the neighborhood of 21 kHz.

Figure 2:
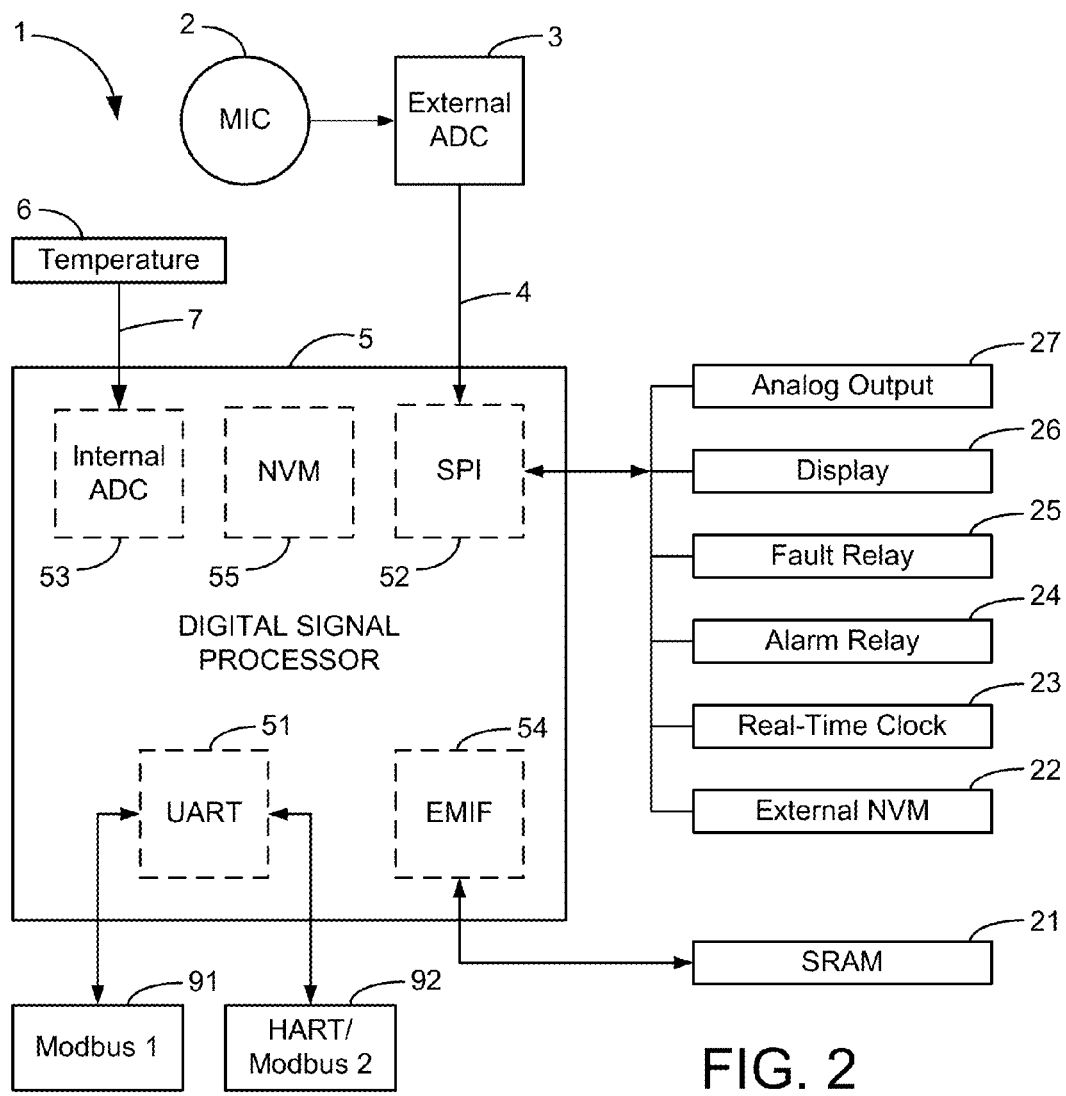
FIG. 2 is a schematic block diagram of an exemplary embodiment of an ultrasonic gas leak detector.

FIG. 2 illustrates a schematic block diagram of an exemplary ultrasonic gas leak detector 1 including an ultrasonic microphone 2 as a sensing element. In an exemplary embodiment, the ultrasonic microphone 2 may be a pre-polarized pressure microphone, such as manufactured by G.R.A.S. Sound and Vibration of Holte, Denmark, Microtech Gefell GmbH of Gefell, Germany, or Bruel Kjaer of Naerum, Denmark. The ultrasonic region is defined as a frequency range beyond human hearing, starting at approximately 20 kHz in healthy, young human adults. Higher ultrasonic frequencies are attenuated more rapidly in air than lower frequencies, and the practical applications for an ultrasonic gas leak detection system are typically for frequencies less than 100 kHz.

In yet another exemplary embodiment, the ultrasonic microphone 2 may be a miniature microphone based on MEMS (Micro Electro Mechanical Systems) technology that can be operated well beyond the audible range of 15 kHz and into the ultrasonic frequency range out to 100 kHz. Such a MEMS microphone may be mounted on a printed circuit board (PCB) and housed in an environmentally robust mechanical enclosure that permits passage of ultrasonic sound energy to the sensing element. An exemplary MEMS microphone that may be used in such fashion is the SiSonic™ Surface Mount Microphone manufactured by Knowles Acoustics of Itasca, Ill. In an exemplary embodiment suitable for operation in a hazardous location, the MEMS microphone may be housed behind a flame arrestor. Such a flame arrestor prevents the transmission of ignited flames from within the microphone housing structure to the external environment while permitting acoustic energy to flow from the external environment to the microphone. Such a method of protection is known as explosion proof or flame proof. Some of the standards that are widely accepted by the industry and government regulatory bodies for explosion proof or flame proof designs are CSA C22.2 No. 30-M1986 from the Canadian Standards Association, FM 3600 and 3615 from Factory Mutual, and IEC 60079-0 and IEC 60079-1 from the International Electrotechnical Commission. Other protection methods may be applied for other environmental protection requirements such as ingress protection against solid objects, liquids, and mechanical impact as described in IEC 60529 from the International Electrotechnical Commission.

Regardless of the microphone type and protection concept utilized, the analog signal generated by the microphone 2 is converted into a digital signal by an analog to digital converter (ADC) 3. In an exemplary embodiment, the ADC 3 provides a signal 4 with 12-bit signed integer resolution and a sampling rate of 200 kHz.

In an exemplary embodiment, the ultrasonic gas leak detector 1 includes an electronic controller 5, e.g., a digital signal processor (DSP), an ASIC or a microcomputer or microprocessor based system. In an exemplary embodiment, the signal processor 5 may comprise a DSP, although other devices or logic circuits may alternatively be employed for other applications and embodiments. In an exemplary embodiment, the signal processor 5 also comprises a dual universal asynchronous receiver transmitter (UART) 51 as a serial communication interface (SCI), a serial peripheral interface (SPI) 52, an internal ADC 53, an external memory interface (EMIF) 54 for an external memory (SRAM) 21, and a non-volatile memory (NVM) 55 for on-chip data storage. Modbus 91 or HART 92 protocols may serve as interfaces for serial communication over UART 51. Both protocols are well-known in process industries, along with others such as PROFIbus, Fieldbus and CANbus, for interfacing field instrumentation to the user's computer or programmable logic controller (PLC).

In an exemplary embodiment, signal processor 5 receives the digital detector signals 4 from the ADC 3 through the SPI 52. In an exemplary embodiment, the signal processor 5 is connected to a plurality of other interfaces through the SPI 52. These interfaces may include an external NVM 22, a real-time clock 23, an alarm relay 24, a fault relay 25, a display 26, and an analog output 27.

In an exemplary embodiment, the analog output 27 may produce an indicative current level between 0 and 20 milliamps (mA), which can be used to trigger a remedial action, such as, by way of example only, shutting down process equipment pursuant to an established facility protocol. A first current level at the analog output 27, for example between 4 mA and 20 mA, may be indicative of a gas leak, a second current level at the analog output 27, for example 4 mA, may be indicative of normal operation, e.g., when no gas leak is present, and a third current level at the analog output 27, for example, 0 mA, may be indicative of a system fault, which could be caused by conditions such as electrical malfunction. In other embodiments, other current levels may be selected to represent various conditions.

In an exemplary embodiment, ultrasonic gas leak detector 1 may also include a temperature sensor 6 for providing a temperature signal 7, indicative of an ambient temperature of the gas detector system for subsequent temperature compensation. The temperature detector 6 may be connected to the internal ADC 53 of the signal processor 5, which converts the temperature signal 7 into a digital representation.

Figure 3:
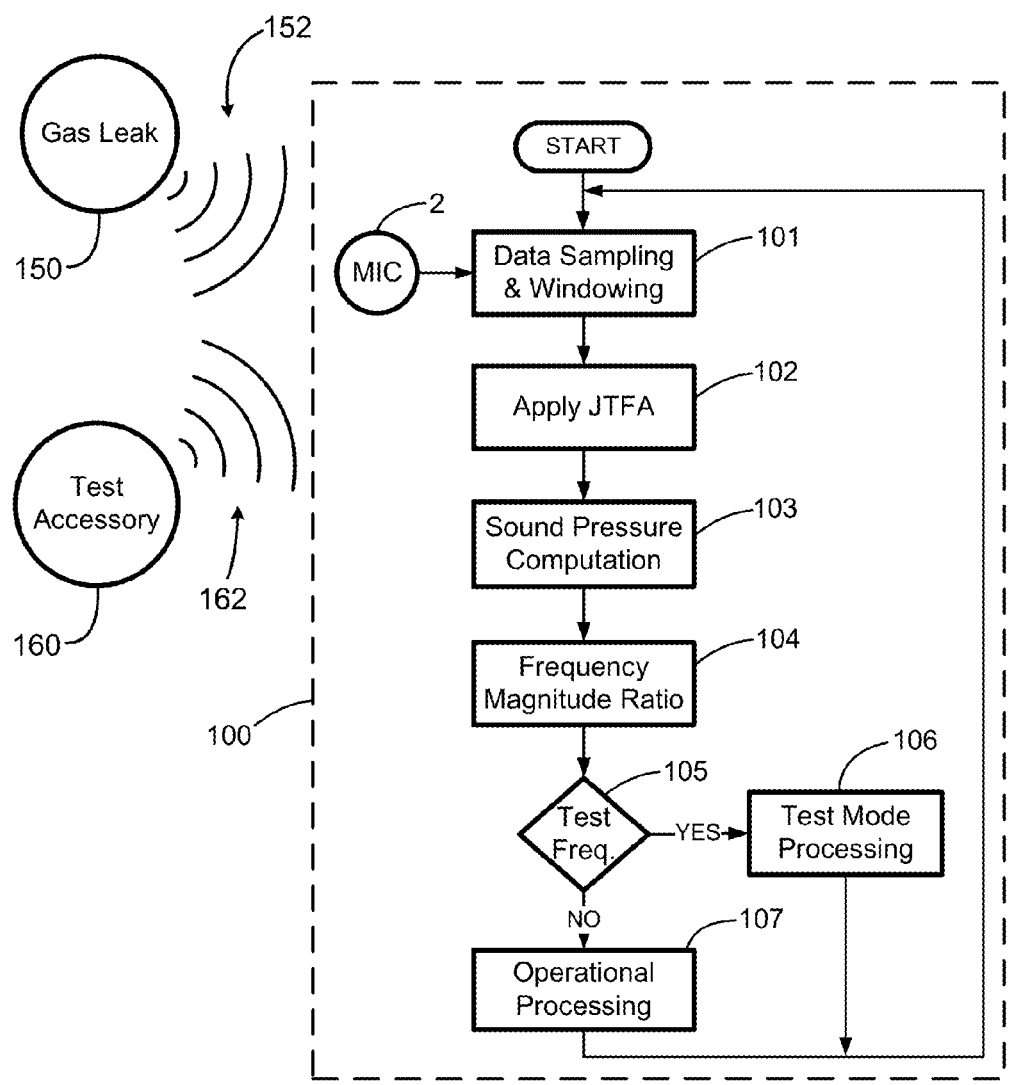
FIG. 3 is an exemplary flow diagram of the processing functions utilized in the ultrasonic gas leak detector of FIG. 1.

Conventional ultrasonic gas leak detectors calculate the total received sound pressure level without performing any frequency spectral analysis. To enable an ultrasonic gas leak detector to identify the signature of a remote ultrasonic test source or a nuisance source such as an electronic dog whistle, frequency analysis 100 is performed (FIG. 3) by signal processor 5. The microphone signal is conditioned electronically for gain and band pass filtered to remove audible frequencies such as, for example, below 15 kHz. The electronic signal is then digitized and a frequency spectrum obtained by applying a Fourier Transform to the time domain signal. Such Fourier Transform may be obtained by, for example, a Joint Time Frequency Analysis (JTFA) after data windowing. Referring to FIG. 3, the data windowing function 101 involves applying one of a Hanning, Hamming, Parzen, rectangular, Gauss, exponential or other appropriate data windowing function. In an exemplary embodiment, the data window function 101 comprises a Hamming window function which is described by a cosine type function:

$$W^{Hm} = \frac{1}{2}\left\{1.08 - 0.92\cos\left(\frac{2\pi n}{N-1}\right)\right\}$$

where N is number of sample points (e.g. 512) and n is between 1 and N.

In an exemplary embodiment, the Hamming window function 101 is applied to the input signal before applying 102 a JTFA function. This data windowing function alleviates spectral "leakage" of the signal as detailed, for example, in Signal Processing for Intelligent Sensor Systems, by David C. Swanson, Marcel Dekker, Inc. 2000. Referring again to FIG. 3, in an exemplary embodiment, JTFA 102 encompasses a Discrete Fourier Transform. The JTFA 102 may also encompass a Short-Time Fourier Transform (STFT) with a shifting time window (also known as Gabor transform), or a Discrete Wavelet Transform (DWT), described in the Swanson reference. The output of the Fourier Transform may be filtered or processed to remove frequency responses outside an ultrasonic frequency band, for example, between about 15 kHz to about 70 kHz.

The sound pressure level (SPL) is computed at 103 by summing over the magnitude of the intensities at the various ultrasonic frequencies selected from the Fourier Transform and normalized by a calibration factor dependent on the microphone sensitivity and electronic gain. The ultrasonic SPL is expressed in decibels (dB), which is a logarithmic measure of the effective pressure of sound relative to a reference value. The commonly used "zero" reference sound pressure (0 dB) in air is 20 µPa RMS, historically derived from the threshold of human hearing. The typical values of ultrasonic SPL in a quiet industrial environment such as remote onshore wellheads may be between 40 dB and 58 dB, while the background ultrasonic SPL can be much higher in the presence of machinery in operation such as compressors, generators and coolers (fin-fans).

Figure 4A:
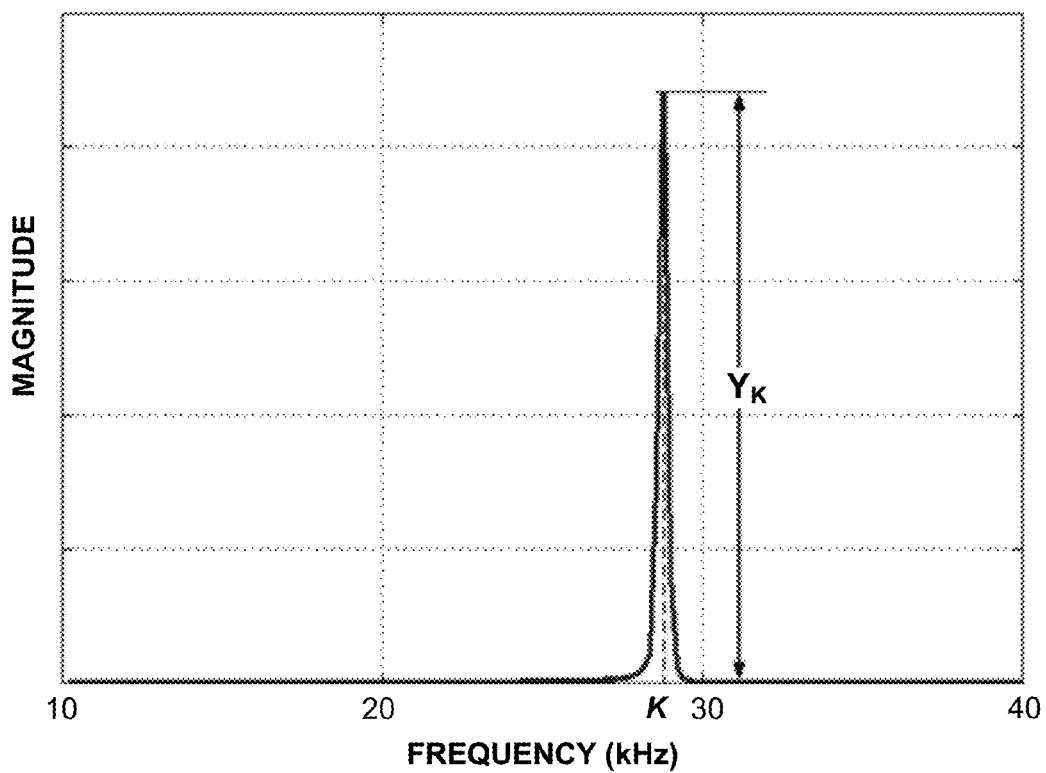
FIG. 4A is an exemplary frequency spectrum of the sound produced by a remote ultrasonic test source.
Figure 4B:
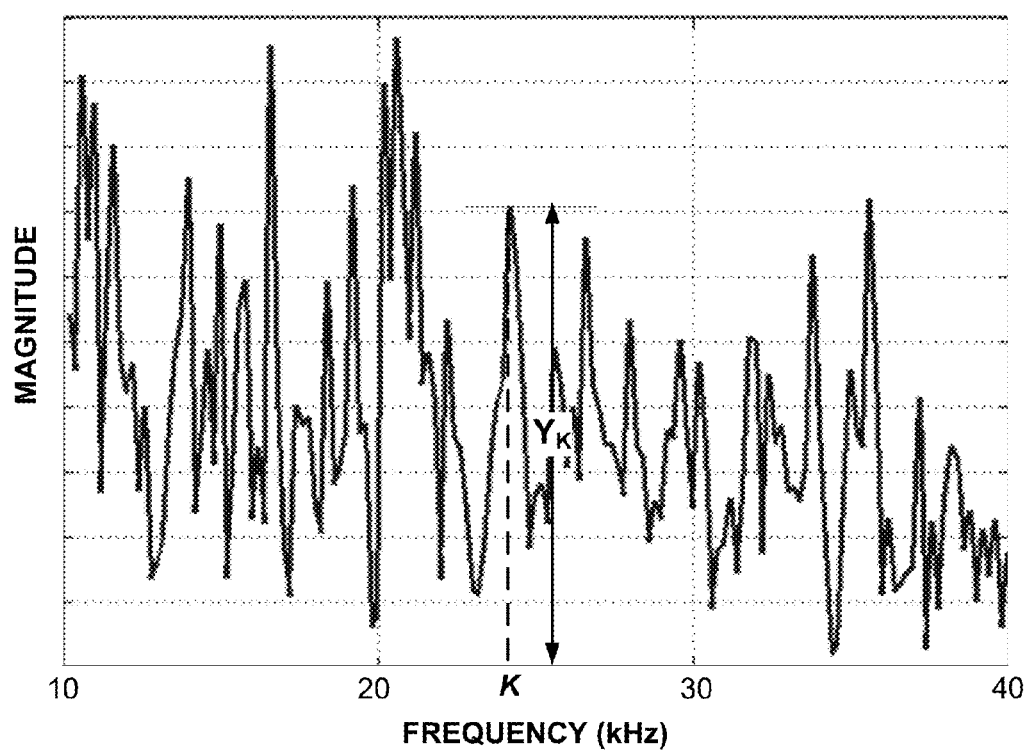
FIG. 4B is an exemplary frequency spectrum of the sound produced by a pressurized gas leaking through an orifice.

FIG. 4A shows the frequency spectrum of an artificial sound source such as a remote ultrasonic test source 160, while FIG. 4B shows the frequency spectrum of broadband energy 152 (FIG. 3) from a broadband ultrasonic source 150 such as a gas leak. US patent application 2012/0194973 A1, the entire contents of which are incorporated herein by this reference, describes the ultrasonic emission characteristics of a remote ultrasonic test source that emits a narrow ultrasonic beam at a single frequency and is designed for use in hazardous locations. A test source as described in this co-pending application is suitable for use in the testing method described herein. Other test sources generating a narrow frequency band or a single frequency may alternatively be employed. Pressurized gas leaking through a restricted opening or orifice produces ultrasonic frequency emissions over a wide range of frequencies, while the remote tester may be designed to produce a single specific frequency or a narrow frequency band signal, as described in US 2012/0194973 A1.

To distinguish and quantify the frequency peak content in the received ultrasound, a mathematical computation 104 (FIG. 3) could be performed. In an exemplary computation, the peak magnitude in a frequency spectrum is compared to the sum of magnitudes of all frequencies. That is, the said ratio would be low in the case of broadband noise and significantly higher in the case of a single peak. The ratio R is described by the following formula:

$$R = \frac{\max(Y_k)}{\sum_{i=0}^{max(k)} Y_i}$$

where $Y_k$ is the magnitude at frequency k.

The frequency location of the peak magnitude in the frequency spectrum identifies the source of the ultrasound as being a remote ultrasonic test source or other nuisance single frequency source such as an electronic dog whistle. In an exemplary embodiment, the remote ultrasonic test source emission frequency could be 30 kHz within a permissible frequency band of +/−1 kHz, i.e., the remote test source is identified as a legitimate ultrasonic test source only if a single tone frequency of 30 kHz+/−1 kHz is detected via frequency spectrum analysis (FIG. 4A). A window of +/−1 kHz is assigned to account for variations in the manufacture of the remote ultrasonic test source or in the purity of the test source signal. In another embodiment, in place of a single test frequency a discrete set of frequencies or a time sequence of frequencies could be used to identify the remote ultrasonic test source. In an exemplary embodiment, the remote ultrasonic test source could switch periodically between two frequencies, for example, 35 kHz and 40 kHz.

At 105 (FIG. 3), the processor determines whether the signal from a test source 2, i.e. generating the test frequency, has been validly detected. If not, the leak detector operates in the normal operating mode (107) to detect gas leaks. Exemplary embodiments of gas detectors with gas detection operating modes are described in co-pending U.S. patent application Ser. No. 13/535,182, filed Jun. 27, 2012, and Ser. No. 13/802,410, filed Mar. 13, 2013, the entire contents of which are incorporated herein by this reference. Other techniques for gas leak detection operation may alternatively be employed.

Figure 3A:
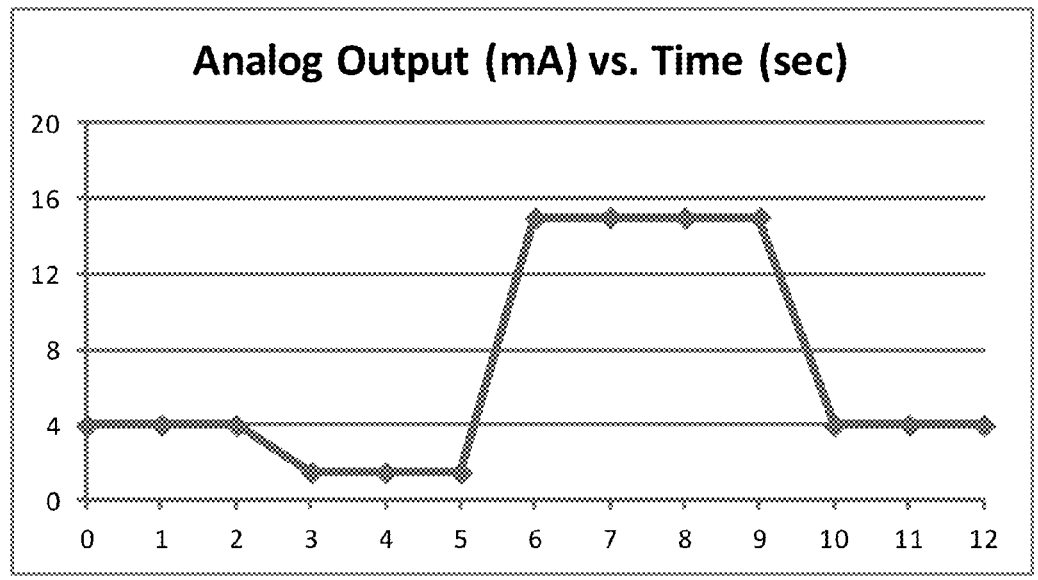
FIG. 3A is a graph illustrating an exemplary detector analog output during a test mode.
Figure 5:
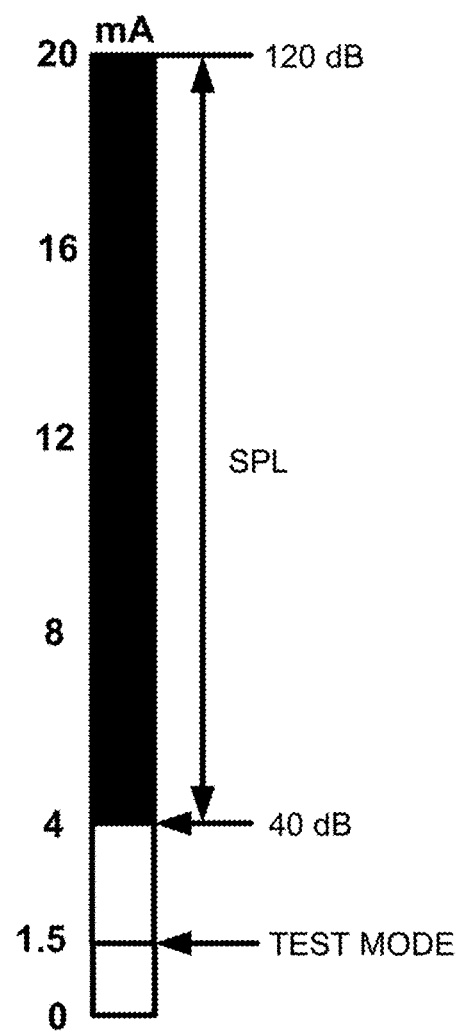
FIG. 5 is an exemplary embodiment of the analog output of an ultrasonic gas leak detector.

Once the ultrasonic gas leak detector identifies at 105 (FIG. 3) the ultrasonic energy as emanating from a remote ultrasonic test source (i.e. a friendly source), it can immediately initialize a test mode 106 whereby the ultrasonic gas leak detector indicates to the outside world the presence of a test source rather than a gas leak. In an exemplary embodiment, illustrated in FIGS. 3A and 5, this indication can take the form of the analog output 27 (0 to 20 mA) of the ultrasonic gas leak detector being set to 1.5 mA for 2 seconds, signaling to the user that it has entered a test mode. Analog output current levels (see FIG. 5) between 0 and 4 mA are used to indicate states such as test mode or faults. In an exemplary embodiment, the user would disable his alarm system for a period of time, or until the remote ultrasonic test source is switched off or pointed away from the ultrasonic gas leak detector. When the latter occurs, the ultrasonic gas leak detector resumes normal operational processing 107 (FIG. 3), which is primarily its function of gas detection.

Figure 3B:
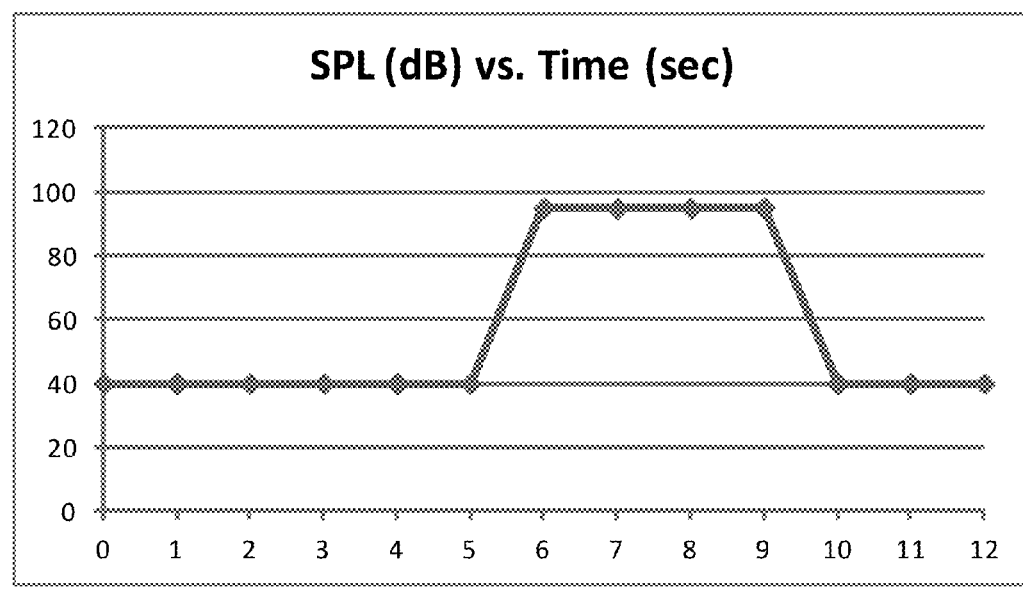
FIG. 3B is a graph illustrating the detector measured sound pressure level (SPL) during the test mode of FIG. 3A.

While the ultrasonic gas leak detector is in test mode 106, the SPL computed may be compared against what is to be expected from the ultrasound energy generated by the remote test unit, for example, 95 dB at 5 meters distance. FIG. 3B illustrates the SPL indicated on local display 26 (FIG. 3) of the detector 1 during an exemplary test mode sequence. During the test mode, the ultrasonic gas leak detector outputs SPL on the analog output 27 after initially indicating test mode initiation by, for example, dropping to 1.5 mA for 2 seconds. In an exemplary embodiment, an analog output of 4 mA represents 40 dB while the maximum of 20 mA represents 120 dB, the highest SPL the ultrasonic gas leak detector may measure. If the measured SPL does not match the expected SPL, for example, 95 dB at 5 meters distance, the test person would know the ultrasonic gas leak detectors is not functioning properly. A reduced SPL reading may, for example, indicate blockage by dirt or moisture of the microphone windscreen protector of the detector, leading to maintenance and retest. The measurement of SPL may be indicated by local display 26 on the detector 1, so the test person could view the SPL during test without the need to monitor the analog output 27.

The method of calculating the ratio of peak to total ultrasonic energy described above can be used to reject as hostile or nuisance other single frequency sources such as the electronic dog whistle mentioned earlier. That is, ultrasonic sound sources that do not emit within the frequency band or pattern of the legitimate remote ultrasonic tester can be rejected as false alarms, as opposed to being confused with real pressurized gas leaks as happens with conventional ultrasonic gas leak detectors. Thus, for a remote ultrasonic test source that operates at a single frequency, the criteria for identifying at 105 (FIG. 3) the remote test source and initiating the test mode 106 within the ultrasonic gas leak detector, in an exemplary embodiment, could be $R > R_{threshold}$ where $R_{threshold}$ is a ratio previously established as adequate to signal the presence of a single ultrasonic frequency, and $SPL > SPL_{threshold}$ where $SPL_{threshold}$ is a threshold value such as 79 dB, and (30 kHz−1 kHz)$<f_{detected}<$(30 kHz+1 kHz), where $f_{detected}$ is the peak frequency obtained from the frequency spectral analysis.

In this exemplary embodiment, all three of the above criteria (ratio threshold, SPL threshold, and peak frequency range) would need to be met simultaneously for a predetermined time, for example 2 seconds, in order for the ultrasonic gas leak detector to enter test mode 106. It is therefore highly unlikely that test mode initiation could happen accidently. It would also be very difficult for mischief makers or saboteurs to intentionally set an ultrasonic gas leak detector into the test mode unless they were in possession of an authentic remote ultrasonic test source pointed towards an ultrasonic gas leak detector configured to detect it.

Ultrasonic gas leak detectors with features as described above provide maintenance personnel with a means to functionally remote test the gas leak detector at proof test intervals without the disruption caused by the need to disable alarms.

Although the foregoing has been a description and illustration of specific embodiments of the subject matter, various modifications and changes thereto can be made by persons skilled in the art without departing from the scope and spirit of the invention.

The invention claimed is:

1. A method of testing an ultrasonic gas leak detector, comprising:
    operating the gas leak detector in an operating mode, wherein the gas leak detector is responsive to broadband ultrasonic energy generated by a pressurized gas leak to initiate an alarm mode;
    ensonifying the gas leak detector with ultrasonic energy from a remote test source which is different from the broadband ultrasonic energy generated by a real gas leak, the remote test source being a separate device from the ultrasonic gas leak detector and wherein the remote test source is not under control of the gas leak detector;
    with the gas leak detector in the operating mode, processing the received ultrasonic energy to determine if measured characteristics of the ultrasonic energy correspond to predetermined characteristics of a predetermined test signal from a test source; and
    initializing a test mode of the gas leak detector if the processing indicates the received ultrasonic energy is a test signal from the test source, including generating an output signal from the gas leak detector indicating that the gas leak detector is operating in the test mode and not in the operating mode for gas leak detection.

2. The method of claim 1, wherein the step of operating the gas leak detector in a test mode includes:
    measuring a sound pressure level (SPL) of the received test ultrasonic energy;
    comparing the measured SPL of the test signal to an expected SPL.

3. The method of claim 1, wherein the test signal is a narrowband ultrasonic sound.

4. The method of claim 3, wherein the step of processing the received ultrasonic energy comprises:
    obtaining an ultrasonic frequency spectrum of the received signal reflecting spectral signal components and magnitudes of the received signal;
    determining a peak signal component magnitude and the frequency of the peak signal component magnitude;
    comparing the peak signal magnitude to a sum of magnitudes of all signal components;
    determining that the received signal is not a test signal if a ratio of the peak signal magnitude does not exceed a predetermined threshold value.

5. The method of claim 4, wherein the step of processing the received ultrasonic energy further comprises:
    determining that the received ultrasonic energy is not a test signal if the sound pressure level of the received energy does not exceed a predetermined sound pressure level threshold.

6. The method of claim 5, wherein the step of processing the received ultrasonic energy further comprises:
    comparing the frequency of the peak signal magnitude to a predetermined test frequency or test frequency range and determining that the received ultrasonic energy is not a test signal if the frequency of the peak signal magnitude does not correspond to the predetermined test frequency or test frequency range.

7. The method of claim 1, wherein the remote test source is a portable device, and said ensonifying the gas leak detector with ultrasonic energy from a remote test source comprises:
    moving the portable remote test source about the gas leak detector from a distance to test the gas leak detector from different directions.

8. An ultrasonic gas leak detector configured to discriminate ultrasound generated by a pressurized gas leak into the atmosphere from ultrasound generated by man-made ultrasonic sources, comprising:
    an ultrasonic microphone system responsive to received ultrasonic energy to generate microphone signals;
    a processor system responsive to the microphone signals and configured to enter an alarm mode during an operating mode in response to microphone signals indicative of a high pressure gas leak, and to identify ultrasonic test signals from a remote ultrasonic test source as a known test source and to initiate a test mode in response to identification of the test signal instead of entering an alarm mode, and wherein the remote ultrasonic test source is a separate device from the gas leak detector and the remote ultrasonic test source is not under control of the gas leak detector;
    the processor system configured to provide an output function to generate detector outputs in dependence on the test mode initiation, said detector outputs indicating that the gas leak detector is operating in the test mode and not in the operating mode.

9. The gas leak detector of claim 8, wherein the processor system is further configured to process the microphone signals to identify other man-made ultrasonic sources as being neither gas leaks nor remote test sources but as nuisance or hostile sources.

10. The gas leak detector of claim 8, wherein the test signals are single frequency or narrowband test signals at a predetermined test source frequency or narrow frequency band.

11. The gas leak detector of claim 8, wherein the processor system is further configured to resume the operating mode from the test mode when the remote test signals are no longer received from the remote test source, the remote test source being switched off or pointed away from the gas leak detector.

12. An ultrasonic gas leak detector configured to discriminate the ultrasound generated by a pressurized gas leak into the atmosphere from ultrasound generated by man-made ultrasonic sources, comprising:

an ultrasonic microphone system responsive to received ultrasonic energy to generate microphone signals;

a processor system configured to process digitized versions of the microphone signals, and:

in an operating mode, to process the digitized versions to detect pressurized gas leaks and initiate an alarm mode upon detection;

the processor system further configured to identify unique ultrasonic test signals from a remote ultrasonic test source as a known test source and to initiate a test mode in response to the identification instead of entering an alarm mode, and wherein the remote test source is a separate device and not under control of the gas leak detector;

the processor system configured to provide an output function to generate detector outputs in dependence on the test mode initiation, said detector outputs indicating that the gas leak detector is operating in the test mode and not in the operating mode.

13. The gas leak detector of claim 12, wherein the processor system is further configured to process the microphone signals to identify other ultrasonic sources as being neither gas leaks nor remote test sources but as nuisance or hostile sources.

14. The gas leak detector of claim 12, wherein the test signals are single frequency or narrowband test signals at a predetermined test source frequency or narrow frequency band.

15. The gas leak detector of claim 14, wherein the processor system is further configured to:

process said digitized signals to provide an ultrasonic frequency spectrum of the received signal, reflecting spectral signal components and magnitudes of the microphone signals;

determine a peak signal component magnitude and a frequency of the peak signal component magnitude;

determine that the received signal is not the unique test signal if a ratio of the peak signal magnitude to a sum of magnitudes of all signal components does not exceed a predetermined threshold value.

16. The gas leak detector of claim 15, wherein the processor system is further configured to measure the sound pressure level of the received ultrasonic energy and to determine that the received ultrasonic energy is not the unique test signal if the measured sound pressure level does not exceed a predetermined sound pressure level threshold.

17. The gas leak detector of claim 12, wherein the processor system is further configured to process the digitized signals to provide an ultrasonic frequency spectrum of the received signal, reflecting spectral signal components and magnitudes of the microphone signals, and to compare the frequency of the peak signal magnitude to a predetermined test frequency or test frequency range and determining that the received ultrasonic energy is not the unique test signal if the frequency of the peak signal magnitude does not correspond to the predetermined test frequency or test frequency range.

18. The gas leak detector of claim 12, wherein the processor system is further configured to resume the operating mode from the test mode when the remote test signals are no longer received by the gas leak detector from the remote test source, the remote test source being switched off or pointed away from the gas leak detector.

* * * * *